United States Patent [19]
Mobley et al.

[11] Patent Number: 5,389,360
[45] Date of Patent: Feb. 14, 1995

[54] ORAL COMPOSITIONS

[75] Inventors: Michael J. Mobley, Cincinnati; Michael F. Lukacovic, West Chester; Peter A. Padolik, Mason; Gregory Berry, Cincinnati, all of Ohio

[73] Assignee: The Procter & Gamble Company, Cincinnati, Ohio

[21] Appl. No.: 96,535

[22] Filed: Jul. 22, 1993

Related U.S. Application Data

[63] Continuation-in-part of Ser. No. 61,138, May 13, 1993, abandoned.

[51] Int. Cl.$^6$ .................. A61K 7/16; A61K 33/34
[52] U.S. Cl. ........................... 424/49; 424/630
[58] Field of Search ..................... 424/49–58, 424/630

[56] References Cited

U.S. PATENT DOCUMENTS

| | | | |
|---|---|---|---|
| 4,180,473 | 12/1979 | Maurer et al. | 252/182 |
| 4,278,610 | 7/1981 | Maurer et al. | 260/438.1 |
| 4,332,791 | 6/1982 | Raaf et al. | 424/52 |
| 4,652,444 | 3/1987 | Maurer | 424/49 |
| 4,708,864 | 11/1987 | Maurer | 424/49 |
| 4,795,628 | 1/1989 | Afseth | 424/54 |
| 4,824,661 | 4/1989 | Wagner | 424/52 |
| 4,863,898 | 9/1989 | Ashmead et al. | 514/6 |
| 5,286,479 | 2/1994 | Garlich et al. | 424/54 |
| 5,292,538 | 3/1994 | Paul et al. | 426/74 |
| 5,298,237 | 3/1994 | Fine | 424/49 |

*Primary Examiner*—Sher K. Rose
*Attorney, Agent, or Firm*—Douglas C. Mohl; David K. Dabbiere; Jacobus C. Rasser

[57] ABSTRACT

Disclosed are oral compositions such as toothpastes, mouthrinses, liquid dentifrices, lozenges and gums containing copper bis-glycinate.

7 Claims, No Drawings

ORAL COMPOSITIONS

This is a continuation-in-part of application Ser. No. 08/061,138, filed on May 13, 1993, now abandoned.

TECHNICAL FIELD

The present invention relates to oral compositions which provide antiplaque and antigingivitis benefits as well as being effective against other anaerobic infections of the mouth.

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

The use of copper compounds in oral products is disclosed in a number of references. One such reference is U.S. Pat. No. 4,332,791 Jun. 1, 1982 to Raaf et al. Raaf et al. describe combinations containing copper salts in dentifrice compositions employing a silica abrasive.

Another reference disclosing copper compounds is U.S. Pat. No. 4,652,444, Mar. 14, 1987, to Maurer. The specific copper compound disclosed is mono copper citrate which releases copper in accordance with a sigmoidally shaped curve.

It has now been found that copper bis-glycinate provides a very good performance profile and is effective against diseases of the oral cavity such as plaque, gingivitis and periodontitis.

It is therefore an object of the present invention to provide improved products containing copper bis-glycinate.

It is a further object of the present invention to provide more effective products for treating diseases of the oral cavity.

It is still a further object to provide methods for treating diseases of the oral cavity.

It is also an object of the present invention to provide products which are effective against bad breath.

These and other objects will become readily apparent from the disclosure which follows.

All percentages and ratios used herein are by weight unless otherwise specified. Also, all measurements referred to herein are made at 25° C. in the composition unless otherwise specified.

SUMMARY OF THE INVENTION

The present invention, in certain aspects, embraces compositions containing a copper bis-glycinate as an antibacterial agent.

The present invention also encompasses a method for treating diseases of the oral cavity using the specified compositions.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the materials perform their intended functions.

By the term "pharmaceutically acceptable carrier", as used herein, is meant a suitable vehicle which can be used to apply the present actives in the oral cavity.

DETAILED DESCRIPTION OF THE INVENTION

The present invention in certain aspects involves oral compositions containing copper bis-glycinate. The essential and optional components are set forth below.

COPPER BIS-GLYCINATE

Copper bis-glycinate is the primary active ingredient used in the compositions of the present invention. Copper bis-glycinate can be purchased as the salt and has the structural formula:

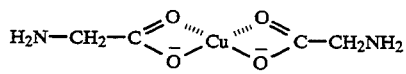

Copper bis-glycinate can also be formed in-situ by using appropriate salts of copper and glycine. Suitable copper compounds which supply copper ions are, in principle, all copper compounds being toxicologically harmless, compatible with mucous membranes and, to some extent, water-soluble.

The following inorganic copper salts may be used: Copper chloride, $CuCl_2$, and the dihydrate thereof; copper fluoride, $CuF_2$ and the dihydrate thereof; copper fluorosilicate, $CuSiF_6$, and the hexahydrate thereof; copper sulphate, $CuSO_4$, and the pentahydrate thereof; copper nitrate and the tri- and hexa-hydrates thereof; and also less popular copper salts, such as copper bromide, $CuBr_2$; copper metaborate, $Cu(BO_2)_2$; copper bromate, $Cu(BrO_3)_2$; copper chlorate; $Cu(ClO_3)_2$, 6-$H_2O$; copper iodate, $Cu(IO_3)_2$, and copper fluorophosphate, $CuPO_3F$.

Suitable sources of glycine besides glycine itself include sodium glycinate, potassium glycinate and glycine hydrochloride.

"Copper bis-glycinate" as the term is used herein includes ratios of copper and glycine differing somewhat from one part copper to two parts glycine. The ratios of copper to glycine which are most useful herein are as follows:

Preferred about 1:1.5 to about 1:3.5;
More preferred about 1:1.8 to about 1:3.0;
Most preferred about 1:1.8 to about 1:2.4.

Copper bis-glycinate is used in an amount sufficient to provide from about 1 to about 8000, preferably from about 25 to about 6000, most preferably from about 50 to about 4000 ppm copper ions. For dentifrices the preferred levels are from about 200 to about 8000 ppm, more preferably from about 400 to about 6000 ppm, and most preferably from about 800 to about 4000 ppm. For rinses the levels are preferably from about 25 to about 1000 ppm, more preferably from about 50 to about 750 ppm, and most preferably from about 100 to about 500 ppm. For lozenges and chewing gums levels as low as about 1 ppm copper are effective.

PHARMACEUTICALLY ACCEPTABLE CARRIER

The carrier for the active ingredient(s) herein can be any composition suitable for use in the oral cavity. Such compositions include toothpastes, mouthrinses, liquid dentifrices, lozenges, chewing gums or other vehicles suitable for use in the oral cavity. Toothpaste and mouthrinses are the preferred systems.

The abrasive polishing material contemplated for use in the toothpaste compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For these reasons they are preferred for use herein.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the toothpaste compositions described herein is present at a level of from about 6% to 70%, preferably from about 15% to about 25%.

Flavoring agents can also be added to toothpaste compositions. Suitable flavoring agents include oil of wintergreen, oil of peppermint, oil of spearmint, oil of sassafras, and oil of cloves. Sweetening agents which can be used include aspartame, acesulfame, saccharin, dextrose, levulose and sodium cyclamate. Flavoring and sweetening agents are generally used in toothpastes at levels of from about 0.005% to about 2% by weight.

Toothpaste compositions can also contain emulsifying agents. Suitable emulsifying agents are those which are reasonably stable and foam a wide pH range, including non-soap anionic, nonionic, cationic, zwitterionic and amphoteric organic synthetic detergents. Many of these suitable agents are disclosed by Gieske et al. in U.S. Pat. No. 4,051,234, Sep. 27, 1977, incorporated herein by reference. The emulsifying agents are present at a level of from about 0.5% to about 2.0%.

Water is also present in the toothpastes of this invention. Water employed in the preparation of commercially suitable toothpastes should preferably be deionized and free of organic impurities. Water generally comprises from about 10% to 50%, preferably from about 30% to 50%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents in an amount from 0.2% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Another preferred embodiment of the present invention is a mouthwash composition. Conventional mouthwash composition components can comprise the carrier for the agents of the present invention. Mouthwashes generally comprise from about 20:1 to about 2:1 of a water/ethyl alcohol solution or be alcohol free and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 5% to 20%) ethyl alcohol, 0% to 20% (preferably 5% to 20%) of a humectant, 0% to.2% (preferably 0.01% to 1.0%) emulsifying agents, 0% to 0.5% (preferably 0.005% to 0.06%) sweetening agent such as saccharin, 0% to 0.3% (preferably 0.03% to 0.3%) flavoring agent, and the balance water. Other optional components described herein earlier for use in toothpaste products are also useful in the mouthwash composition.

Suitable lozenge and chewing gum components are disclosed in U.S. Pat. No. 4,083,955, Apr. 11, 1978 to Grabenstetter, incorporated herein by reference in its entirety.

An additional optional ingredient for use in the compositions of the present invention is a soluble fluoride ion source. Such sources include sodium fluoride, stannous fluoride, sodium monofluorophosphate and are used in amounts sufficient to provide from about 10 to about 3500 ppm $F^-$.

Other optional components are non-cationic water insoluble agents such as triclosan. Such materials are disclosed in U.S. Pat. No. 4,022,889, to Vinson et al., incorporated herein by reference in its entirety.

The pH of the present compositions and/or the pH in the mouth can be any pH which is safe for the mouth's hard and soft tissues. Such pH's are generally from about 3 to about 10, preferably from about 4 to about 8. Buffers may be added to maintain this pH. Such buffers should, however, not complex with copper ions in a manner such that the functioning of the compositions of this invention is hindered.

A method of manufacture for the present compositions is found in the examples.

COMPOSITION USE

The present compositions are used in a conventional manner wherein the amounts of product are what users generally use.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES 1–4

Given below are four dentifrice examples representative of the present invention.

| Component | Ex. 1 | Ex. 2 | Ex. 3 | Ex. 4 |
|---|---|---|---|---|
| | \multicolumn{4}{c}{Weight %} | | | |

| Component | Ex. 1 | Ex. 2 | Ex. 3 | Ex. 4 |
|---|---|---|---|---|
| Sorbitol (70% Solution) | 61.827 | 61.827 | 51.827 | 56.827 |
| Glycerine | — | — | 10.000 | — |
| Glycine | 0.218 | 0.218 | 0.262 | 0.184 |
| Copper (II) Sulfate 5H$_2$O | 0.360 | 0.360 | 0.360 | 0.252 |
| Sodium Fluoride | 0.243 | 0.243 | 0.243 | 0.243 |
| Saccharin | 0.130 | 0.130 | 0.130 | 0.320 |
| Titanium Dioxide | 0.525 | 0.525 | 0.525 | 0.525 |
| FD&C Blue | 0.050 | 0.050 | 0.050 | 0.050 |
| Silica | 20.000 | 20.000 | 20.000 | 25.000 |
| Carboxy Methyl Cellulose | — | 0.750 | — | — |
| Xanthan Gum | 0.475 | — | 0.475 | 0.475 |
| Carbopol 956* | 0.300 | — | 0.300 | 0.300 |
| Flavor | 0.900 | 0.900 | 0.900 | 1.100 |
| Sodium Alkyl Sulfate (28% Solution) | 4.000 | — | 4.000 | 4.000 |
| Sodium Lauroyl Sarcosinate (28% Solution) | — | 4.000 | — | — |
| Water | 10.973 | 10.977 | 10.900 | 10.755 |

*Carboxyvinyl polymer offered by B. F. Goodrich Company.

EXAMPLES 5–8

Given below are four rinse examples representative of the present invention.

| Component | Ex. 5 | Ex. 6 | Ex. 7 | Ex. 8 |
|---|---|---|---|---|
| Undenatured Alcohol | 16.250 | 16.250 | 16.250 | 11.250 |
| Polysorbate 80* | 0.120 | 0.120 | 0.120 | 0.120 |
| Glycerine | 10.000 | 10.000 | 10.000 | 15.000 |
| Glycine | 0.060 | 0.144 | 0.072 | 0.060 |
| Copper (II) Sulfate-5H$_2$O | 0.100 | 0.200 | 0.100 | 0.100 |
| Saccharin | 0.060 | 0.060 | 0.060 | 0.060 |
| Flavor | 0.150 | 0.100 | 0.150 | 0.120 |
| Water | 73.260 | 73.150 | 73.240 | 73.290 |

*Polyoxyethylene (20) sorbitan monooleate.

EXAMPLE 9

Given below is a lozenge example of the present invention.

| Component | Weight % |
|---|---|
| Sorbitol | 17.5 |
| Mannitol | 17.5 |
| Starch | 13.6 |
| Glycine | 0.007 |
| Copper (II) Sulfate .5H$_2$O | 0.010 |
| Saccharin | 0.25 |
| Flavor | 1.50 |
| Corn Syrup | Balance |

EXAMPLE 10

Given below is a chewing gum example of the present invention.

| Component | Weight % |
|---|---|
| Gum Base | 30.0 |
| 30 parts Estergum | |
| 45 parts Coumorone Resin | |
| 15 parts Dry Latex | |
| Sugar | 50.0 |
| or for sugarless gum replace sugar with: | |
| Sorbitol | 49.75 |
| Nutrasweet or Saccharin | 0.25 |
| Corn Syrup | 18.47 |
| Glycine | 0.014 |
| Copper (II) Sulfate .5H$_2$O | 0.020 |
| Flavor | 1.50 |

What is claimed is:

1. An oral composition effective against diseases of the oral cavity comprising:
   (a) a safe and effective amount of copper bis-glycinate; and
   (b) a pharmaceutically acceptable carrier.

2. A composition according to claim 1 wherein the concentration of copper bis-glycinate is sufficient to provide from about 1 to about 8000 parts per million copper ions.

3. A composition according to claim 2 which is in the form of a mouthrinse.

4. A composition according to claim 3 which in addition contains a humectant and ethanol.

5. A method of treating diseases of the oral cavity by applying to said cavity a safe and effective amount of a composition according to claim 1.

6. A method of treating diseases of the oral cavity by applying to said cavity a safe and effective amount of a composition according to claim 3.

7. A method of treating diseases of the oral cavity by applying to said cavity a safe and effective amount of a composition according to claim 4.

* * * * *